United States Patent [19]

Weinkauf

[11] 4,138,610
[45] Feb. 6, 1979

[54] TOMOGRAPHIC X-RAY APPARATUS FOR PRODUCING TRANSVERSE LAYER IMAGES

[75] Inventor: Burghard Weinkauf, Erlangen, Fed. Rep. of Germany

[73] Assignee: Siemens Aktiengesellschaft, Berlin & Munich, Fed. Rep. of Germany

[21] Appl. No.: 787,854

[22] Filed: Apr. 15, 1977

[30] Foreign Application Priority Data

Jun. 18, 1976 [DE] Fed. Rep. of Germany ....... 2627433

[51] Int. Cl.² ............................................. G03B 41/16
[52] U.S. Cl. .................................. 250/445 T; 250/402
[58] Field of Search .................... 250/445 T, 401, 402

[56] References Cited

U.S. PATENT DOCUMENTS 3,946,234  3/1976  Hounsfield ....................... 250/445 T Primary Examiner—Craig E. Church
Attorney, Agent, or Firm—Hill, Gross, Simpson, Van Santen, Steadman, Chiara & Simpson

[57] ABSTRACT

In the illustrated embodiment, a series of detectors subject to additive errors in measurement due to high voltage variations is provided with a reference channel having a detector or an equivalent component which is not exposed to the radiation, but which is responsive to high voltage fluctuations. The output from the reference channel during each measurement cycle is supplied to multiplier circuitry which receives from each channel as a second input a stored constant representing the deviation in sensitivity of the channel detector as compared to the reference detector or equivalent. The output from the multiplier is combined with the measured value from such channel by means of a subtractor circuit so as to correct the output from the channel for the errors introduced by fluctuations in the high voltage supply.

4 Claims, 3 Drawing Figures

TOMOGRAPHIC X-RAY APPARATUS FOR PRODUCING TRANSVERSE LAYER IMAGES

BACKGROUND OF THE INVENTION

The invention relates to a tomographic x-ray apparatus for producing transverse layer images of a radiographic subject, with an x-ray measuring arrangement comprising an x-ray source producing a fan-shaped x-ray beam penetrating the radiography subject, the crosssectional extent of this beam, perpendicular to the layer plane, being equal to the layer thickness, and, in the layer plane, being of such a magnitude that the entire radiographic subject is penetrated, said measuring arrangement further including a radiation receiver which determines the intensity of radiation behind the subject, with a drive system for the measuring arrangement for producing rotational movements, and with a measured value converter for the transformation of the signals supplied by the radiation receiver into a layer image, wherein the radiation receiver consists of a series of detectors, these detectors being connected at one terminal to a common power supply installation, and the number of detectors being selected in accordance with the desired picture resolution (or definition).

It is known to employ as a measured value source for the measured value converter, xenon-detectors connected to a high voltage source and functioning as ionization chambers. Thus, per angular position of measuring arrangement (1, 2), all image points of the angular position are simultaneously measured via a corresponding number of individual x-ray detectors, and the signals of the detectors are further processed in parallel in individual measuring channels. In a measuring arrangement such as this, various types of errors occur; one type being the so-called additive errors in measurement brought about by high voltage instability. In utilizing xenon-detectors, every change in the common operating high voltage produces a displacement current due to the detector capacitance. This displacement current is superimposed on the x-ray measuring signal as an additive error. Particularly interfering are those high voltage changes which do not die down again or which only die down incompletely during the measuring interval, since, subsequent to differentiation at the detector capacitance, these interferences have as a consequence displacement currents which are not or are only partially cancelled out.

SUMMARY OF THE INVENTION

The object which is the basis of the invention consists in producing a tomographic x-ray apparatus of the type initially cited wherein there is a substantially complete compensation of the additive errors described, so that there can be an increase in the measurement accuracy and a decrease in the demand for stability of the operating high voltage of the detector.

In accordance with the invention, this object is achieved in that there is provided a reference channel with a detector, or an equivalent component, not exposed to the x-radiation, that there is provided for each measuring channel a multiplier for multiplying the output signal of the reference channel with a constant representing the deviation in sensitivity of the channel detector from the reference detector, or the equivalent component, respectively, and that, in addition, a subtracter for the output signal of the measuring channel and of the multiplier is present for each measuring channel. In the subject of the invention, the output signal of the subtracter is essentially free of errors brought about by fluctuations in the operating voltage of the detectors.

Other objects, features and advantages of the invention will be apparent from the following detailed description taken in connection with the accompanying sheet of drawings.

DETAILED DESCRIPTION

Figure 1:
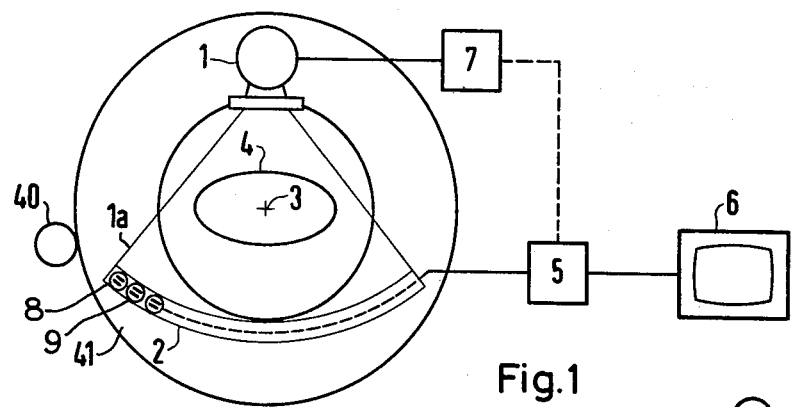
FIG. 1 is a diagrammatic illustration of tomographic x-ray apparatus having a measured value converter system in accordance with the present invention applied thereto.
Figure 2:
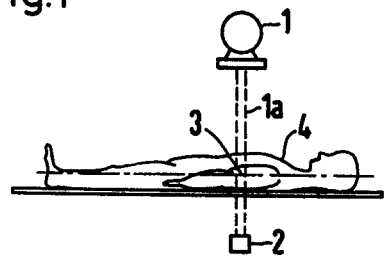
FIG. 2 is a diagrammatic longitudinal view illustrating the relationship of the measuring arrangement of FIG. 1 to a patient.

FIGS. 1 and 2 schematically illustrate a known tomographic x-ray apparatus of this type. From FIG. 1, it is apparent that the fan-shaped x-ray beam 1a being issued from x-ray tube 1 has an angular extent such as to comprehend radiographic subject 4; i.e., it simultaneously penetrates the entire patient cross section in the illustrated layer plane. FIG. 2 illustrates that the x-ray beam 1a, perpendicular to the layer plane, is equal to the layer thickness. The tomographic x-ray apparatus according to FIGS. 1 and 2 includes the x-ray tube 1 emitting x-ray beam 1a and a radiation receiver 2 manifesting, on the order of magnitude, over 100, for example, 256 individual detectors arranged in a series. Radiation receiver 2 has a curved formation with a center of curvature at the focus of x-ray tube 1. The measuring arrangement 1, 2, is rotatable about an axis 3 disposed in radiographic subject 4. The number of detectors of radiation receiver 2 is selected in accordance with the desired picture resolution (or definition), so that an image can be calculated by a measured value converter 5 on the basis of one rotation of measuring arrangement 1, 2. Rotation proceeds by means of an electric motor 40 (FIG. 1) which engages with a rotating ring 41 on which the x-ray tube 1 and the radiation receiver 2 are mounted. The image is reproduced on a display unit 6. X-ray tube 1 is pulsed during the rotation of measuring arrangement 1, 2, in specific angular positions; for example, after each angular degree of rotation, the pulsation proceeding for such a short time that blurring caused by the rotation remains sufficiently small. In order to do this, x-ray generator 7 for x-ray tube 1 is momentarily switched on for the purpose of pulsating the x-ray tube 1. The measured values of radiation receiver 2 occur in synchronism with the pulse operation of the x-ray source. Such synchronization of the turn-on of generator 7 and readout from detector 2 is indicated by the dash line between components 5 and 7.

Figure 3:
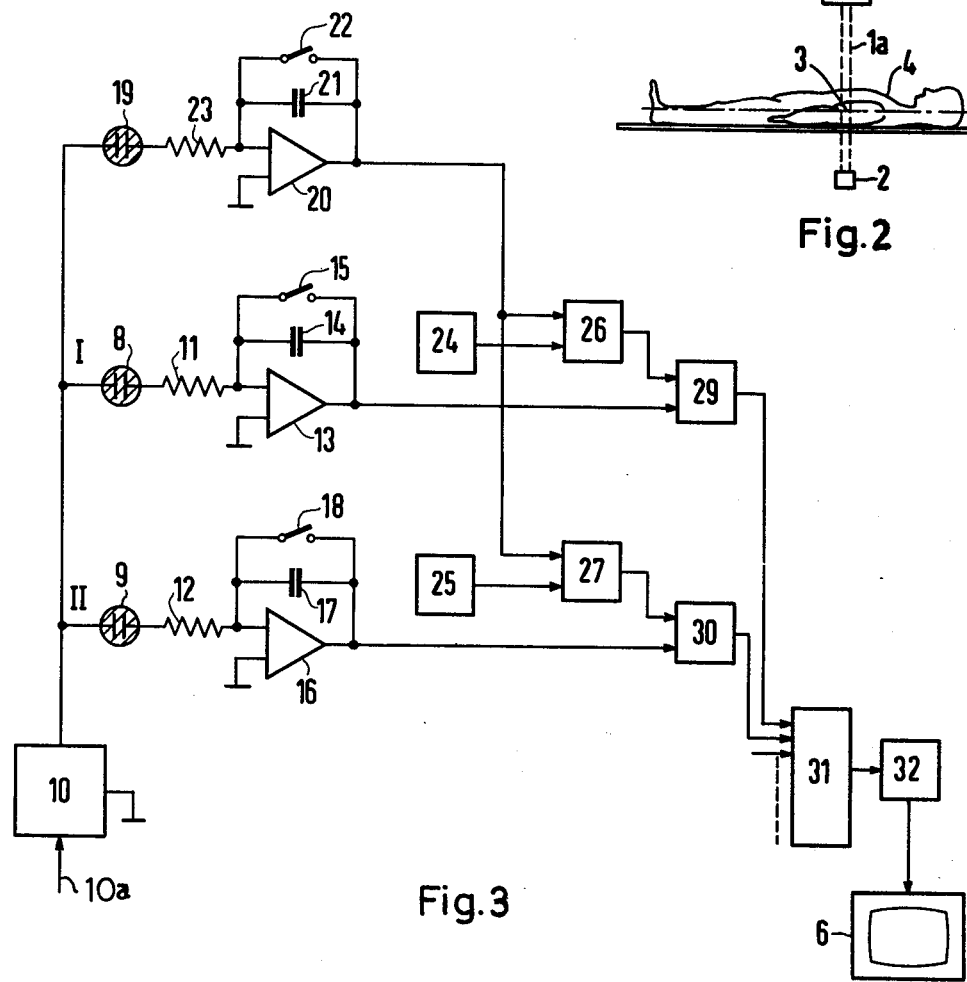
FIG. 3 is a detailed electric circuit diagram showing a preferred embodiment in accordance with the present invention.

FIG. 3 illustrates two measuring channels from radiation receiver 2 having two xenon-detectors 8 and 9. As already explained, there are more of these xenon detectors present (as indicated in FIG. 1), in fact, a number corresponding to the desired picture resolution (or definition). However, the individual channels of the xenon detectors are of a similar construction so that the invention can be explained only on the basis of two channels. All xenon-detectors are connected at one terminal thereof to a high voltage supply installation 10 and, at the other terminal, to an integrator via a current limiting resistance, of which FIG. 2, illustrates current limiting resistances 11 and 12. The integrator of channel I contains an amplifier 13, an integration capacitor 14, and a quenching switch 15. The integrator of channel II contains an amplifier 16, an integration capacitor 17, and a quenching switch 18. Quenching switches 15, 18, etc., have the task of quenching integrators 13, 14; 16, 17; etc., when their signals have been processed to complete a measurement cycle.

In addition to the measuring channels, a reference channel is also present with a xenon detector 19, an integrator 20, 21, and a quenching switch 22. Xenon detector 19 is not exposed to x-radiation in any position of the measuring arrangement 1, 2. An equivalent capacitor may also be used in its place. It is coupled to integration amplifier 20 via a current limiting resistance 23.

In order to eliminate the additive errors described, a trigger pulse is sent once by means of a pulse producer connected to the high voltage supply installation 10 by means of input 10a. This pulse may be manually initiated, and effects a change in the high voltage; for example, an increase in the high voltage. The output signals of all measuring channels I, II, etc., and of the reference channel, brought about on account of the change in the high voltage, are measured. For each measuring channel, the quotient is formed from the output voltage of the measuring channel, brought about in this manner, and from the output voltage of the reference channel. This quotient represents a constant K which characterizes the deviation of the channel detector from the reference detector 19 and which does not change in the course of operation. This constant is placed into a constant-memory (or store) for each channel. The constant-memory (or store) of channel I is designated by 24, and the constant-memory (or store) of channel II is designated by 25.

Each measuring channel contains a multiplier 26, 27, etc., which multiplies the channel constant K with the output signal of the reference channel occurring during the x-ray measuring cycle. Thus, at the output of each multiplier there is an error voltage characterizing the error of the channel which can be attributed to high voltage fluctuations. If the error voltage is subtracted in a subtracter 29, 30, etc., from the output voltage of the measuring channel during a measurement cycle, the output signal of the subtracter is then free of errors caused by high voltage fluctuations. Each measuring channel has a subtracter for this purpose.

The outputs of all the subtracters are connected to a time multiplexer 31, which consecutively interrogates the output signals of subtracters 29, 30, etc., of the individual channels, and delivers the corresponding signals to a calculator 32 which calculates the crosssectional image and effects its reproduction on display unit 6. Components 11 through 32 are thus component parts of the measured value converter 5.

Within the framework of the invention, it is not necessary for each measuring channel to contain one multiplier and one subtracter each. It is also conceivable to provide only one multiplier and one subtracter for all the measuring channels and to switch these components over to the individual channels by means of a time multiplexer.

It will be apparent that many modifications and variations may be effected without departing from the scope of the novel concepts and teachings of the present invention.

I claim as my invention:

1. Tomographic x-ray apparatus for producing transverse layer images of a radiographic subject, including an x-ray measuring arrangement which comprises an x-ray source producing a fan-shaped x-ray beam penetrating the radiographic subject, and a radiation receiver which determines the radiation intensity behind the subject; including a drive system for the measuring arrangement in order to produce rotational movements; and including a measured value converter for the transformation of the signals supplied by the radiation receiver into a layer image; the radiation receiver having a series of detectors, these detectors being arranged for connection at one terminal thereof with a common power supply, and the number of detectors being selected in accordance with the desired picture resolution and having their output signals sampled during each measurement cycle; characterized in that a reference channel is present, having reference response means not exposed to the x-radiation and providing a reference output signal responsive to power supply fluctuations during each measurement cycle, and having a response substantially similar to the response of the detectors of said series with respect to power supply fluctuations, the measuring channels having a multiplier means for multiplying the output signal of the reference channel with a constant representing the deviation in sensitivity of each channel detector from the reference response means, and that, in addition, there is present for each measuring channel a subtracter for the output signal of each measuring channel and of the multiplier means, such that the output of each subtracter is corrected for power supply fluctuations occurring between successive measurement cycles.

2. Tomographic x-ray apparatus according to claim 1 wherein the reference response means comprises a reference detector similar to the detectors of said series but clear of exposure to said x-ray beam from said x-ray source.

3. A measurement system for tomographic x-ray apparatus for producing transverse layer images of a radiographic subject, such apparatus including an x-ray measuring arrangement which comprises an x-ray source, a radiation receiver, and means operable to produce a series of x-ray exposures of the layer at different angles thereto; and including a measured value converter for the transformation of the signals supplied by the radiation receiver into a layer image; the radiation receiver having a series of detectors for connection at one terminal thereof with a common power supply, the detectors having their output signals sampled during each measurement cycle; characterized in said measurement system comprising a reference channel having reference response means not exposed to the x-radiation during operation of the apparatus and providing a reference output signal responsive to power supply fluctuations during each measurement cycle, and having a response substantially similar to the response of the detectors of said series with respect to power supply fluctuations, measuring channels having multiplier means for multiplying the output signal of the reference channel with a constant representing the deviation in sensitivity of each channel detector from the reference response means, and each measuring channel having a subtracter for the output signal of each measuring channel and of the multiplier means, such that the output of each subtracter is corrected for power supply fluctuations occurring between successive measurement cycles.

4. A measuring system according to claim 3 with the reference response means comprising a reference detector similar to the detectors of said series but clear of exposure to said x-ray beam from said x-ray source throughout the entire operation of the tomographic apparatus.

* * * * *